US012082948B2

(12) United States Patent
Jang et al.

(10) Patent No.: US 12,082,948 B2
(45) Date of Patent: Sep. 10, 2024

(54) APPARATUS AND METHOD FOR GENERATING BLOOD PRESSURE ESTIMATION MODEL, AND APPARATUS FOR ESTIMATING BLOOD PRESSURE

(71) Applicants: SAMSUNG ELECTRONICS CO., LTD., Suwon-si (KR); University of Maryland, College Park, College Park, MD (US)

(72) Inventors: Dae Geun Jang, Yongin-si (KR); Peyman Yousefian, Quincy, MA (US); Jin-Oh Hahn, Potomac, MD (US); Ui Kun Kwon, Hwaseong-si (KR); Youn Ho Kim, Hwaseong-si (KR); Sungtae Shin, Busan (KR)

(73) Assignees: SAMSUNG ELECTRONICS CO., LTD., Suwon-si (KR); University of Maryland, College Park, College Park, MD (US)

( * ) Notice: Subject to any disclaimer, the term of this patent is extended or adjusted under 35 U.S.C. 154(b) by 478 days.

(21) Appl. No.: 17/322,458

(22) Filed: May 17, 2021

(65) Prior Publication Data
US 2021/0393214 A1  Dec. 23, 2021

Related U.S. Application Data

(60) Provisional application No. 63/040,099, filed on Jun. 17, 2020.

(30) Foreign Application Priority Data

Aug. 20, 2020  (KR) ........................ 10-2020-0104529

(51) Int. Cl.
*A61B 5/00* (2006.01)
*A61B 5/021* (2006.01)
(Continued)

(52) U.S. Cl.
CPC ........ *A61B 5/7278* (2013.01); *A61B 5/02125* (2013.01); *A61B 5/1102* (2013.01);
(Continued)

(58) Field of Classification Search
CPC ............ A61B 5/02125; A61B 5/02416; A61B 5/0245; A61B 5/1102; A61B 5/352;
(Continued)

(56) References Cited

U.S. PATENT DOCUMENTS 9,011,346 B2   4/2015  Wiard et al.
9,241,637 B2   1/2016  Wiard et al.
(Continued)

FOREIGN PATENT DOCUMENTS

KR       10-1576665 B1    12/2015
KR    10-2016-0146393 A   12/2016
(Continued)

OTHER PUBLICATIONS

Brannick, Regression with Two Independent Variables, University of South Florida, Apr. 3, 2018 (Year: 2018).*
(Continued)

*Primary Examiner* — Kyle R Quigley
(74) *Attorney, Agent, or Firm* — Sughrue Mion, PLLC

(57) ABSTRACT

An apparatus for generating a blood pressure estimation model includes: a signal acquirer configured to receive input a first signal and a second signal from a user; and a processor configured to obtain a pulse transit time (PTT) as a first predictor variable value based on the first signal and the second signal, to extract at least one feature from the second signal, to obtain a second predictor variable value based on the extracted at least one feature, and to generate a blood pressure estimation model based on the first predictor variable value and the second predictor variable value.

11 Claims, 14 Drawing Sheets

(51) Int. Cl.
  *A61B 5/11* (2006.01)
  *A61B 5/352* (2021.01)
  *G16H 50/50* (2018.01)
  *A61B 5/024* (2006.01)
  *A61B 5/0245* (2006.01)

(52) U.S. Cl.
  CPC ............ *A61B 5/352* (2021.01); *A61B 5/7275* (2013.01); *G16H 50/50* (2018.01); *A61B 5/02416* (2013.01); *A61B 5/0245* (2013.01)

(58) Field of Classification Search
  CPC .... A61B 5/7275; A61B 5/7278; G16H 40/63; G16H 50/30; G16H 50/50
  See application file for complete search history.

(56) References Cited

U.S. PATENT DOCUMENTS

| | | | |
|---|---|---|---|
| 10,045,700 | B2 | 8/2018 | Noh et al. |
| 10,420,470 | B2 | 9/2019 | Kwon et al. |
| 10,478,082 | B2 | 11/2019 | Kim et al. |
| 2012/0203077 | A1 | 8/2012 | He et al. |
| 2015/0018637 | A1* | 1/2015 | Chen .................... A61B 5/0295 600/301 |
| 2016/0220122 | A1* | 8/2016 | Luna .................... A61B 5/1102 |
| 2016/0361029 | A1 | 12/2016 | Kang et al. |
| 2017/0042433 | A1* | 2/2017 | Noh .................... A61B 5/14542 |
| 2017/0172431 | A1 | 6/2017 | Kim et al. |
| 2017/0209053 | A1 | 7/2017 | Pantelopoulos et al. |
| 2017/0281024 | A1 | 10/2017 | Narasimhan et al. |
| 2018/0177465 | A1 | 6/2018 | Kwon et al. |
| 2018/0235487 | A1* | 8/2018 | Paul .................... A61B 5/02416 |
| 2018/0289288 | A1* | 10/2018 | Kim .................... A61B 5/02108 |
| 2019/0082972 | A1* | 3/2019 | Tao .................... A61B 5/1102 |
| 2019/0254524 | A1* | 8/2019 | Granqvist ............ A61B 5/0024 |
| 2019/0274552 | A1 | 9/2019 | Jang et al. |
| 2019/0365231 | A1 | 12/2019 | Kwon et al. |
| 2020/0107744 | A1 | 4/2020 | Kim et al. |
| 2020/0330050 | A1* | 10/2020 | Peters .................... A61B 5/349 |
| 2020/0405159 | A1* | 12/2020 | Archdeacon ......... A61B 5/7278 |

FOREIGN PATENT DOCUMENTS

| | | |
|---|---|---|
| KR | 10-2017-0004607 A | 1/2017 |
| KR | 10-2017-0019189 A | 2/2017 |
| KR | 10-2017-0073051 A | 6/2017 |
| KR | 10-2018-0076806 A | 7/2018 |
| WO | 2019/206818 A1 | 10/2019 |
| WO | 2019/227468 A1 | 12/2019 |

OTHER PUBLICATIONS

Cai et al., Using impedance plethysmography, IEEE, 2017 (Year: 2017).*

Liu et al., Smart Wearables in Healthcare, JHE, Oct. 2018 (Year: 2018).*

Secerbegovic et al., Blood pressure estimation using video plethysmography, IEEE, 2016 (Year: 2016).*

* cited by examiner

APPARATUS AND METHOD FOR GENERATING BLOOD PRESSURE ESTIMATION MODEL, AND APPARATUS FOR ESTIMATING BLOOD PRESSURE

CROSS-REFERENCE TO RELATED APPLICATION(S)

This application is based on and claims priority under 35 U.S.C. § 119 to Korean Patent Application No. 10-2020-0104529, filed on Aug. 20, 2020, in the Korean Intellectual Property Office, and U.S. Provisional Application No. 63/040,099, filed on Jun. 17, 2020, in the United States Patent and Trademark Office, the entire disclosures of which are herein incorporated by reference for all purposes.

BACKGROUND

1. Field

Example embodiments of the disclosure relate to generating a blood pressure estimation model and estimating blood pressure by using the blood pressure estimation model.

2. Description of the Related Art

As the society is rapidly aging, healthcare technology has attracted much attention to solve problems such as the increase in medical expenses. Accordingly, not only medical devices for use in hospitals or medical examination institutions, but small medical devices that individuals can carry are also being developed. Furthermore, the small medical devices are worn by users in the form of wearable devices capable of directly measuring cardiovascular health status such as blood pressure and the like, thereby enabling users to directly measure and manage their cardiovascular health condition. In order to provide devices in a compact size with improved accuracy in estimating bio-information, much research has been conducted recently on methods of estimating bio-information by analyzing bio-signals.

SUMMARY

Provided are an apparatus and a method for generating a blood pressure estimation model by pulse transit time (PTT) analysis and pulse wave analysis (PWA) using a ballistocardiogram (BCG) signal, and estimating blood pressure by using the blood pressure estimation model without a cuff.

In accordance with an aspect of an example embodiment, there is provided an apparatus for generating a blood pressure estimation model, the apparatus including: a signal acquirer configured to receive a first signal and a second signal of a user; and a processor configured to obtain a pulse transit time (PTT) as a first predictor variable value based on the first signal and the second signal, configured to extract at least one feature from the second signal, configured to obtain a second predictor variable value based on the extracted at least one feature and a reference blood pressure, and configured to generate a blood pressure estimation model based on the first predictor variable value and the second predictor variable value.

The signal acquirer may include a first sensor configured to measure the first signal from the user; and a second sensor configured to measure the second signal from the user.

The apparatus may further include a communication interface, wherein the signal acquirer is further configured to receive at least one of the first signal and the second signal from an external device through the communication interface.

The first signal may include at least one of an electrocardiography (ECG) signal, a photoplethysmogram (PPG) signal, an electromyography (EMG) signal, an impedance plethysmogram (IPG) signal, a pressure wave, and a video plethysmogram (VPG) signal; and the second signal may include a ballistocardiogram (BCG) signal.

The processor may be further configured to: based on the first signal being a PPG signal and the second signal being a BCG signal, obtain, as the PTT, a time interval between an onset point of the PPG signal and any one of a J-wave, an H-wave, an I-wave, a K-wave, and an L-wave of the BCG signal, or the processor may be further configured to, based on the first signal being an ECG signal and the second signal being the BCG signal, obtain, as the PTT, a time interval between an R-wave of the ECG signal and any one of the J-wave, the H-wave, the I-wave, the K-wave, and the L-wave of the BCG signal.

The at least one feature may include at least one of an I-J time interval, a J-L time interval, an I-K time interval, a J-K time interval, a J-K amplitude, a K-L amplitude, and an I-J amplitude of the second signal.

The processor may be further configured to preprocess the first signal and the second signal.

The processor may be further configured to normalize the reference blood pressure, the first predictor variable value, and the at least one feature.

The processor may be further configured to generate a predictor variable acquisition model based on the reference blood pressure, the first predictor variable value, and the at least one feature, and obtain the second predictor variable value by using the predictor variable acquisition model.

The processor may be further configured to generate a residual reference blood pressure by removing a component, which is related to the first predictor variable value, from the reference blood pressure, and generate the predictor variable acquisition model based on the residual reference blood pressure.

The processor may be further configured to remove the component, which is related to the first predictor variable value, by subtracting a value, obtained by calculating an inner product of the reference blood pressure and the first predictor variable value, from the reference blood pressure.

The processor may be further configured to generate the predictor variable acquisition model by using singular value decomposition (SVD) based on the residual reference blood pressure and the at least one feature.

The processor may be further configured to perform singular value decomposition of a component, which is obtained by calculating an inner product of the residual reference blood pressure and the at least one feature, so that a covariance between the residual reference blood pressure and the at least one feature is maximized.

The processor may be further configured to (i) generate a residual reference blood pressure by removing a component, which is related to the first predictor variable value, from the reference blood pressure, (ii) generate a predictor variable acquisition model by using singular value decomposition (SVD) based on the residual reference blood pressure and the at least one feature, and (iii) obtain the second predictor variable value by using the predictor variable acquisition model, and the processor may be further configured to determine the residual reference blood pressure as a next reference blood pressure and repeatedly perform operations (i)-(iii), until a predetermined number of second predictor variable values are obtained.

In accordance with an aspect of an example embodiment, there is provided a method of generating a blood pressure estimation model, the method including: receiving a first signal and a second signal of a user; obtaining a pulse transit time (PTT) as a first predictor variable value based on the first signal and the second signal; extracting at least one feature from the second signal; obtaining a second predictor variable value based on the first predictor variable value and the extracted at least one feature and a reference blood pressure; and generating a blood pressure estimation model based on the first predictor variable value and the second predictor variable value.

The obtaining the second predictor variable value may include normalizing the reference blood pressure, the first predictor variable value, and the at least one feature.

The obtaining the second predictor variable value may include: generating a predictor variable acquisition model based on the reference blood pressure, the first predictor variable value, and the at least one feature; and obtaining the second predictor variable value by using the predictor variable acquisition model.

The generating the predictor variable acquisition model may include generating a residual reference blood pressure by removing a component, which is related to the first predictor variable value, from the reference blood pressure.

The generating the residual reference blood pressure may include removing the component, which is related to the first predictor variable value, by subtracting a value, obtained by calculating an inner product of the reference blood pressure and the first predictor variable value, from the reference blood pressure.

The generating the predictor variable acquisition model may include generating the predictor variable acquisition model by using singular value decomposition (SVD) based on the residual reference blood pressure and the at least one feature.

The generating the predictor variable acquisition model may include performing singular value decomposition of a component, which is obtained by calculating an inner product of the residual reference blood pressure and the at least one feature, so that a covariance between the residual reference blood pressure and the at least one feature is maximized.

The obtaining of the second predictor variable value may include: (i) generating a residual reference blood pressure by removing a component, which is related to the first predictor variable value, from the reference blood pressure; (ii) generating a predictor variable acquisition model by using singular value decomposition (SVD) based on the residual reference blood pressure and the at least one feature; (iii) obtaining the second predictor variable value by using the predictor variable acquisition model; and determining the residual reference blood pressure as a next reference blood pressure and repeatedly performing operations (i)-(iii), until a predetermined number of second predictor variable values are obtained.

In accordance with an aspect of an example embodiment, there is provided an apparatus for estimating blood pressure, the apparatus including: a first sensor configured to measure a first signal from a user; a second sensor configured to measure a second signal from the user; and a processor configured to obtain a pulse transit time (PTT) as a first predictor variable value based on the first signal and the second signal, configured to extract at least one feature from the second signal, configured to obtain a second predictor variable value based on the extracted at least one feature by using a predictor variable acquisition model, and configured to estimate blood pressure based on the first predictor variable value and the second predictor variable value by using a blood pressure estimation model.

BRIEF DESCRIPTION OF THE DRAWINGS

The above and other aspects, features, and advantages of certain example embodiments of the disclosure will be more apparent from the following description taken in conjunction with the accompanying drawings.

DETAILED DESCRIPTION

Figure 1:
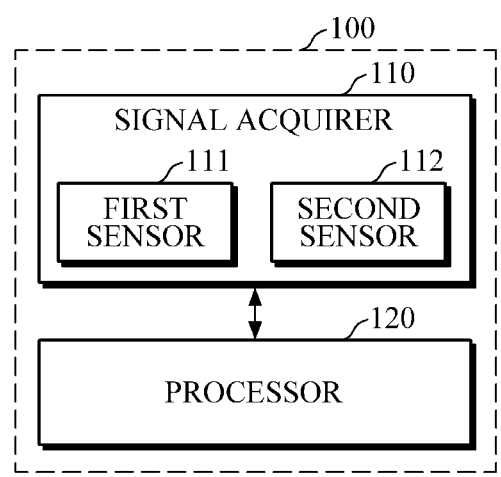
FIGS. 1 and 2 are block diagrams illustrating an apparatus for generating a blood pressure estimation model according to example embodiments.

Details of example embodiments are included in the following detailed description and drawings. Advantages and features of the disclosure, and a method of achieving the same will be more clearly understood from the following example embodiments described in detail with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module,' etc., should be understood as a unit that performs at least one function or operation and that may be embodied as hardware, software, or a combination thereof.

The following description of various example embodiments will be provided using estimation of blood pressure as an example, but the disclosure is not limited thereto, and may be applied to estimation of a variety of bio-information, such as vascular age, arterial stiffness, aortic pressure waveform, stress index, and fatigue level, skin age, skin elasticity, and the like.

Figure 2:
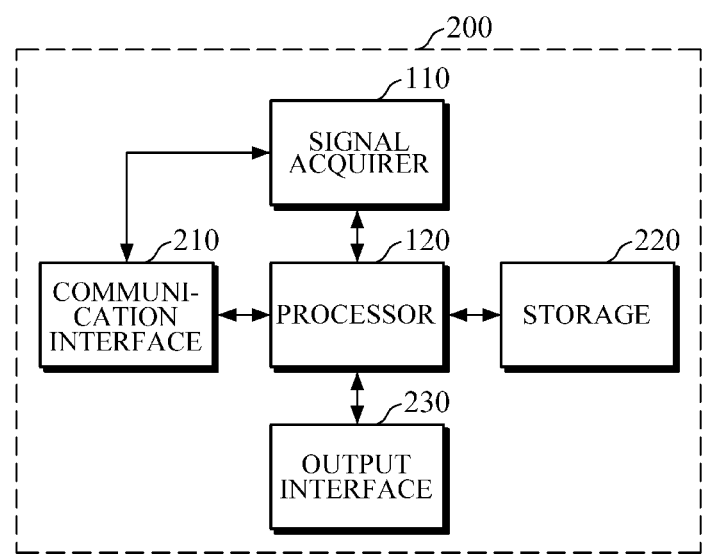

FIGS. 1 and 2 are block diagrams illustrating an apparatus for generating a blood pressure estimation model according to example embodiments.

Referring to FIG. 1, an apparatus 100 for generating a blood pressure estimation model according to an example embodiment includes a signal acquirer 110 and a processor 120.

The signal acquirer 110 includes a first sensor 11 for measuring a first signal from a user, and a second sensor 112 for measuring a second signal from the user. The signal acquirer 110 may measure a plurality of first signals and second signals from a plurality of users by using the first sensor 111 and the second sensor 112, and may transmit the measured plurality of first signals and second signals as training data to the processor 120.

The first sensor 111 may be a photoplethysmogram (PPG) sensor for measuring a photoplethysmogram (PPG) signal. The PPG sensor may include one or more light sources for emitting light onto a user's object and one or more detectors for detecting light reflected or scattered from the object. The light source may include a light emitting diode (LED), a laser diode (LD), a phosphor, and the like. The light source may be formed as one light source or an array of two or more light sources, and may emit light of different wavelengths. Further, the detector may include a photodiode, a phototransistor, a complementary metal-oxide semiconductor (CMOS) image sensor, a charge-coupled device (CCD) image sensor, and the like, and may be formed as one detector or an array of two or more detectors.

However, the first sensor 111 is not limited to the PPG sensor, and may include a sensor for measuring an electrocardiography (ECG) signal, an electromyography (EMG) signal, an impedance plethysmogram (IPG) signal, a pressure wave, a video plethysmogram (VPG) signal, and the like.

The second sensor 112 may be a sensor for measuring a ballistocardiogram (BCG) signal. For example, the second sensor 112 may include various types of sensors for measuring the BCG signal, such as a displacement sensor, a velocity sensor, an acceleration sensor, a load cell sensor, a polyvinylidene fluoride (PVDF) film sensor, an electro mechanical film (EMFi) sensor, a force sensor, and the like. However, the second signal that may be measured by the second sensor 112 is not limited to the BCG signal.

The processor 120 may control the first sensor 111 and the second sensor 112, and may generate a blood pressure estimation model by using the training data received from the first sensor 111 and the second sensor 112. In this case, the processor 120 may further collect, as training data, reference blood pressure values (e.g., systolic blood pressure (SBP), diastolic blood pressure (DBP), mean blood pressure (MBP), pulse pressure (PP), etc.) which are measured from a plurality of users, and may generate a predictor variable acquisition model and a blood pressure estimation model by using the collected training data. For example, the processor 120 may obtain a pulse transit time (PTT) based on the first signal and the second signal, may extract at least one feature based on the second signal, and may generate the predictor variable acquisition model and the blood pressure estimation model by dimension reduction based on the reference blood pressure, the PTT, and the extracted at least one feature. For example, the at least one feature comprises a plurality of features. For illustrative purposes, an example in which a plurality of features are extracted is described; however, the disclosure is not limited thereto.

Referring to FIG. 2, an apparatus 200 for generating a blood pressure estimation model according to an embodiment includes the signal acquirer 110, the processor 120, a communication interface 210, a storage 220, and an output interface 230.

In an example embodiment, at least one of the first sensor 111 and the second sensor 112 of the signal acquirer 110 may be omitted, and may acquire at least one of the first signal and the second signal from an external device through the communication interface 210. Alternatively, the signal acquirer 110 may include both the first sensor 111 and the second sensor 112 as described above, may selectively drive the first sensor 111 or the second sensor 112 under the control of the processor 120, and may control the remaining sensor, which is not driven and mounted in an external device, through the communication interface 210. Examples of the external device may include a smartphone or a wearable device, which has a function of measuring a PPG signal or a BCG signal, or a signal measuring device for separately measuring an ECG signal and the like.

The communication interface 210 may communicate with the external device by using wired and wireless communication techniques under the control of the processor 120, and may receive and transmit a control signal of the processor 120 and/or a signal measured by the external device. Alternatively, in response to a request of an apparatus for estimating blood pressure, the communication interface 210 may periodically or non-periodically transmit the predictor variable acquisition model or the blood pressure estimation model, which is generated by the processor 120, to the apparatus for estimating blood pressure, so that the predictor variable acquisition model or the blood pressure estimation model may be updated.

Examples of the wired and wireless communication techniques include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, the communication techniques are not limited thereto.

The storage 220 may store programs or commands for generating a blood pressure estimation model. Further, the storage 220 may store training data collected from a plurality of users for generating the blood pressure estimation model, and may store the predictor variable acquisition model or the blood pressure estimation model which is generated by the processor 120.

The storage 220 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the storage 220 may include an external storage medium such as web storage and the like.

The output interface 230 may output processing results of the processor 120. For example, the output interface 230 may output the first signal, the second signal, the predictor variable acquisition model, the blood pressure estimation model, and a variety of information related thereto. The output interface 230 may provide a user with the information by using various output modules, such as a display module, a speaker, a haptic module, and the like.

Figure 3:
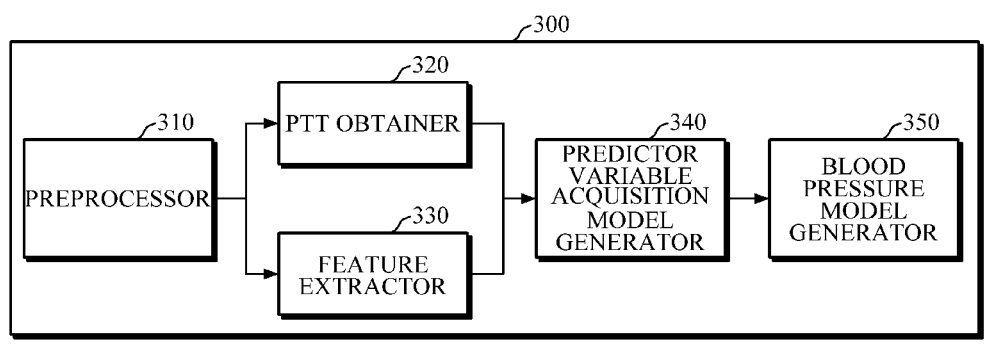
FIG. 3 is a diagram illustrating an example of a processor of FIGS. 1 and 2.
Figure 4:
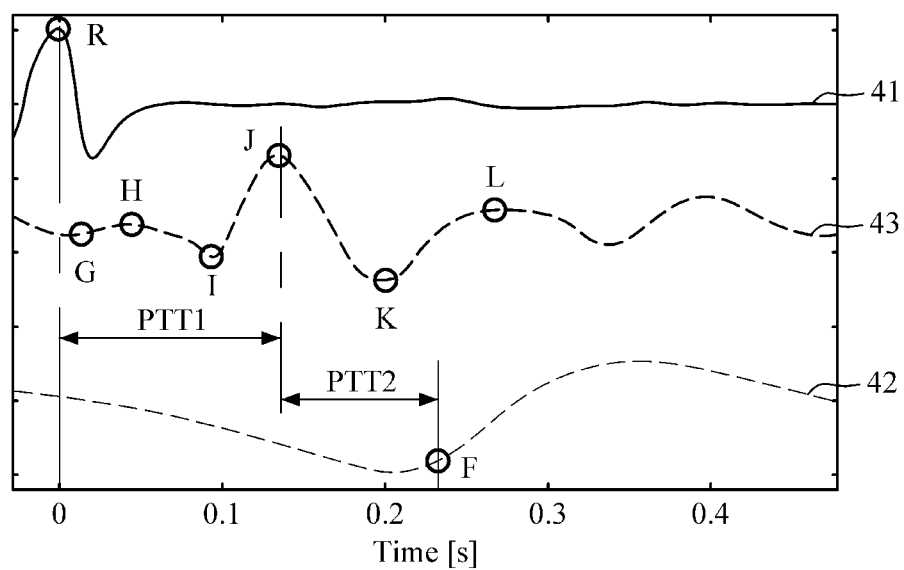
FIG. 4 is a diagram explaining an example of extracting a pulse transit time (PTT) and features.

FIG. 3 is a diagram illustrating an example of a processor of FIGS. 1 and 2. FIG. 4 is a diagram explaining an example of extracting a PTT and features.

Referring to FIG. 3, a processor 300 according to an embodiment includes a preprocessor 310, a PTT obtainer 220, a feature extractor 330, a predictor variable acquisition model generator 340, and a blood pressure estimation model generator 350.

Upon receiving the first signal and the second signal from the signal acquirer 110, the preprocessor 310 may preprocess the first signal and the second signal. For example, the preprocessor 310 may remove noise, such as motion noise, by using various noise removal methods such as filtering, smoothing, and the like. For example, if the first signal is an ECG signal, the preprocessor 310 may perform band-pass filtering with a cutoff frequency of 1 Hz to 40 Hz; and if the first signal is a PPG signal, the preprocessor 310 may perform band-pass filtering with a cutoff frequency of 1 Hz to 10 Hz. Further, if the second signal is a BCG signal, the preprocessor 310 may perform band-pass filtering with a cutoff frequency of 0.8 Hz to 20 Hz.

The PTT obtainer 320 may obtain a PTT as a first predictor variable value based on the first signal and the second signal. For example, the PTT obtainer 320 may extract characteristic points from the first signal and the second signal, and may obtain a time interval between the extracted characteristic points as the PTT. For example, referring to FIG. 4, if the first signal is an ECG signal 41 and the second signal is a BCG signal 43, the PTT obtainer 320 may obtain, as the PTT, a time interval PTT1 between an R-wave (R) of the first signal and a J-wave (J) of the second signal. Alternatively, if the first signal is a PPG signal 42 and the second signal is the BCG signal 43, the PTT obtainer 320 may obtain, as the PTT, a time interval PTT2 between an onset point (F) of the first signal and the J-wave (J) of the second signal. However, the PTT is not limited thereto, and the PTT obtainer 320 may obtain, as the PTT, time intervals between any one of an H-wave, an I-wave, a K-wave, and an L-wave, instead of the J-wave of the BCG signal 43, and the R-wave (R) of the ECG signal 41 and the onset point of the PPG signal 42.

The feature extractor 330 may extract one or more characteristic points from the second signal. For example, as illustrated in FIG. 4, the feature extractor 330 may extract a G-wave (G), an H-wave (H), an I-wave (I), a J-wave (J), a K-wave (K), an L-wave (L), and the like as characteristic points from the BCG signal 42, and may extract features based on the extracted characteristic points. In this case, the feature extractor 330 may obtain one-period signals by performing beat gating on the second signal, and may extract characteristic points from the obtained one-period signals. For example, the feature extractor 330 may segment the one-period signals by performing beat gating on the second signal based on the characteristic point of the first signal. For example, if the first signal is an ECG signal, the feature extractor 330 may perform gating based on the R-wave, and if the first signal is a PPG signal, the feature extractor 330 may perform gating based on a point corresponding to 50% of a heart period compared to an onset point.

Further, by using the extracted characteristic points, the feature extractor 330 may extract, as features, a J-L time interval, an I-K time interval, and a J-K time interval, which are related to a change in PTT, and a J-K amplitude, a K-L amplitude, and an I-J amplitude which are related to a change in pulse pressure (PP). In addition, the feature extractor 330 may extract, as features, a J-J time interval related to a heart rate, i.e., a time interval between a J-wave of a one-period signal and a J-wave of a subsequent one-period signal, and the like.

The predictor variable acquisition model generator 340 may normalize a reference blood pressure, a first predictor variable value, and each feature extracted by the feature extractor 330. By normalization, the predictor variable acquisition model generator 340 may correct a difference in characteristics of each subject (e.g., each user). For example, as shown in Equation 1, the predictor variable acquisition model generator 340 may normalize the values by using an average of the reference blood pressure values, e.g., diastolic blood pressure (DBP) and systolic blood pressure (SBP), the first predictor variable values, and the features, which are measured during a predetermined period of time. However, the normalization is not limited to the following Equation 1, and instead of the average value, the predictor variable acquisition model generator 340 may use a reference blood pressure, a feature, and a PTT, which are obtained at a time when a user is at rest, and may use various other known normalization methods.

$$\tilde{P}^{(i)} = \frac{P^{(i)} - \overline{P}^{(i)}}{\overline{P}^{(i)}}$$ [Equation 1]

$$\tilde{\tau}^{(i)} = \frac{\tau^{(i)} - \overline{\tau}^{(i)}}{\overline{\tau}^{(i)}}$$

$$\tilde{\phi}_k^{(i)} = \frac{\phi_k^{(i)} - \overline{\phi}_k^{(i)}}{\overline{\phi}_k^{(i)}}$$

Herein, $P^{(i)}$ denotes reference blood pressure values of an i-th subject. The reference blood pressure values may be DBP, SBP and PP. $\overline{P}^{(i)}$ denotes an average of the reference blood pressure values, $\tilde{P}^{(i)}$ denotes a normalized value of the reference blood pressure values, and i denotes the i-th subject. In addition, $\phi_k^{(i)}$, $\overline{\phi}_k^{(i)}$, and $\tilde{\phi}_k^{(i)}$ denote k-th features of the i-th subject, an average of the k-th features, and a normalized value of the k-th features, respectively, in which k denotes an index indicative of each extracted feature. Furthermore, $\tau^{(i)}$, $\overline{\tau}^{(i)}$, and $\tilde{\tau}^{(i)}$ denote first predictor variable values of the i-th subject, i.e., PTT values, an average of the PTT values, and a normalized value of the PTT values, respectively. The average of the PTT values refers to an average value of reference blood pressure values, features and PTT values, which are measured during a predetermined period of time.

The predictor variable acquisition model generator 340 may generate a predictor variable acquisition model based on the reference blood pressure, the first predictor variable value, and the features. The reference blood pressure, the first predictor variable value, and the features may be normalized values. For example, the predictor variable acquisition model generator 340 may generate a predictor variable acquisition model for estimating SBP, a predictor variable acquisition model for estimating DBP, and a predictor variable acquisition model for estimating a PP, based on the normalized first predictor variable value and features, and the reference SBP, the reference DBP, and the reference PP, respectively.

The predictor variable acquisition model generator 340 may generate a residual reference blood pressure by removing a blood pressure component, associated with the first predictor variable value, from the reference blood pressure. For example, as represented by the following Equation 2, the predictor variable acquisition model generator 340 may generate the residual reference blood pressure by subtracting a value, obtained by calculating an inner product of the reference blood pressure and the first predictor variable value, from the reference blood pressure.

$$P^\perp \triangleq P - \frac{P^T \tau}{\tau^T \tau} \tau \qquad \text{[Equation 2]}$$

Herein, $P^\perp$ denotes the residual reference blood pressure, and components which are not determined by the PTT, i.e., blood pressure components (SBP, DBP and PP) crossing the PTT at right angles. P denotes a value obtained by integrating the normalized reference blood pressure values (SBP, DBP and PP) of each subject into a reference blood pressure vector; and T denotes a first predictor variable value vector, into which the normalized first predictor variable value (PTT) of each subject is integrated.

$$\frac{P^T \tau}{\tau^T \tau} \tau$$

denotes a component obtained by calculating an inner product of the reference blood pressure (P) and the first predictor variable value (τ).

The predictor variable acquisition model generator 340 may generate a predictor variable acquisition model by performing, for example, principal component analysis (PCA), singular value decomposition, and the like, on features extracted from the second signal. For example, the predictor variable acquisition model generator 340 may perform singular value decomposition on a component, obtained by calculating an inner product of the residual reference blood pressure and each feature, so that a covariance between the residual reference blood pressure and each feature is maximized.

The predictor variable acquisition model generator 340 may obtain a coupling coefficient of each feature by singular value decomposition, and may generate a predictor variable acquisition model based on the obtained coupling coefficient for each feature. The coupling coefficient of each feature may be obtained by learning based on training data, collected from a plurality of subjects, using various learning methods such as machine learning and the like.

For example, the following Equation 3 represents an example of a predictor variable acquisition model.

$$X = \Sigma_{k=1}^{M} v_k \Phi(k) \qquad \text{[Equation 3]}$$

Herein, X denotes a second predictor variable value, $v_k$ denotes a coupling coefficient for a k-th feature, which is obtained by singular value decomposition, and $\Phi(k)$ denotes the k-th feature. By performing the above process for each of reference blood pressure values, DBP, SBP and PP, the predictor variable acquisition model generator 340 may obtain a coupling coefficient of each feature for each reference blood pressure.

Upon generating the predictor variable acquisition model, the predictor variable acquisition model generator 340 may obtain a second predictor variable value by combining each feature, extracted from the second signal by using the predictor variable acquisition model, and the coupling coefficient of each feature.

The blood pressure estimation model generator 350 may obtain a coefficient for each prediction variable by training a blood pressure estimation model, as represented by the following Equation 4, using the first predictor variable values, the second predictor variable values, and the reference blood pressure values of a plurality of subjects as training data. However, the blood pressure estimation model expressed in Equation 4 is merely an example.

$$Y = \alpha A + \beta X + \qquad \text{[Equation 4]}$$

Herein, Y denotes an estimated blood pressure value; A denotes the first predictor variable value; X denotes the second predictor variable value; α, β, and γ denote the coefficients obtained by learning based on training data of a plurality of subjects. By performing the above process for each of DBP, SBP and PP, the blood pressure estimation model generator 350 may generate the blood pressure estimation model for each of the reference blood pressure values, and may estimate DBP, SBP, and the like independently of each other.

In addition, the predictor variable acquisition model generator 340 may obtain a predetermined number of second predictor variable values by performing singular value decomposition in multi-steps. For example, while repeatedly performing the process of generating a residual reference blood pressure by removing a blood pressure component, associated with the first predictor variable value, from the reference blood pressure and obtaining the second predictor variable values by using the residual reference blood pressure, the predictor variable acquisition model generator 340 may perform, starting from the second time of performing this process, the process of obtaining the second predictor variable values by determining the residual reference blood pressure, which is generated in the preceding process, as a new (or next) reference blood pressure. As described above, the predictor variable acquisition model generator 340 may perform the singular value decomposition in multi-steps of generating a first residual reference blood pressure by removing a PTT-related blood pressure component from the reference blood pressure, and generating a second residual reference blood pressure by removing again the PTT-related blood pressure component from the first residual reference blood pressure. In this manner, blood pressure may be estimated more accurately.

The following Equation 5 represents an example of a blood pressure estimation model using the second predictor variable values obtained by performing the singular value decomposition in multi-steps.

$$Y = \alpha A + \beta_1 X_1 + \beta_2 X_2 + \ldots + \beta_n X_n + \gamma \qquad \text{[Equation 5]}$$

Herein, Y denotes an estimated blood pressure value; A denotes the first predictor variable value; $X_1, X_2, \ldots, X_n$ denote the second predictor variable values obtained by performing the singular value decomposition in multi-steps; and α, $\beta_1, \beta_2, \ldots, \beta n$, and γ denote the coefficients obtained by learning using training data of a plurality of subjects, in which $\beta_1, \beta_2, \ldots$, and $\beta n$ may be the same value.

Figure 5:
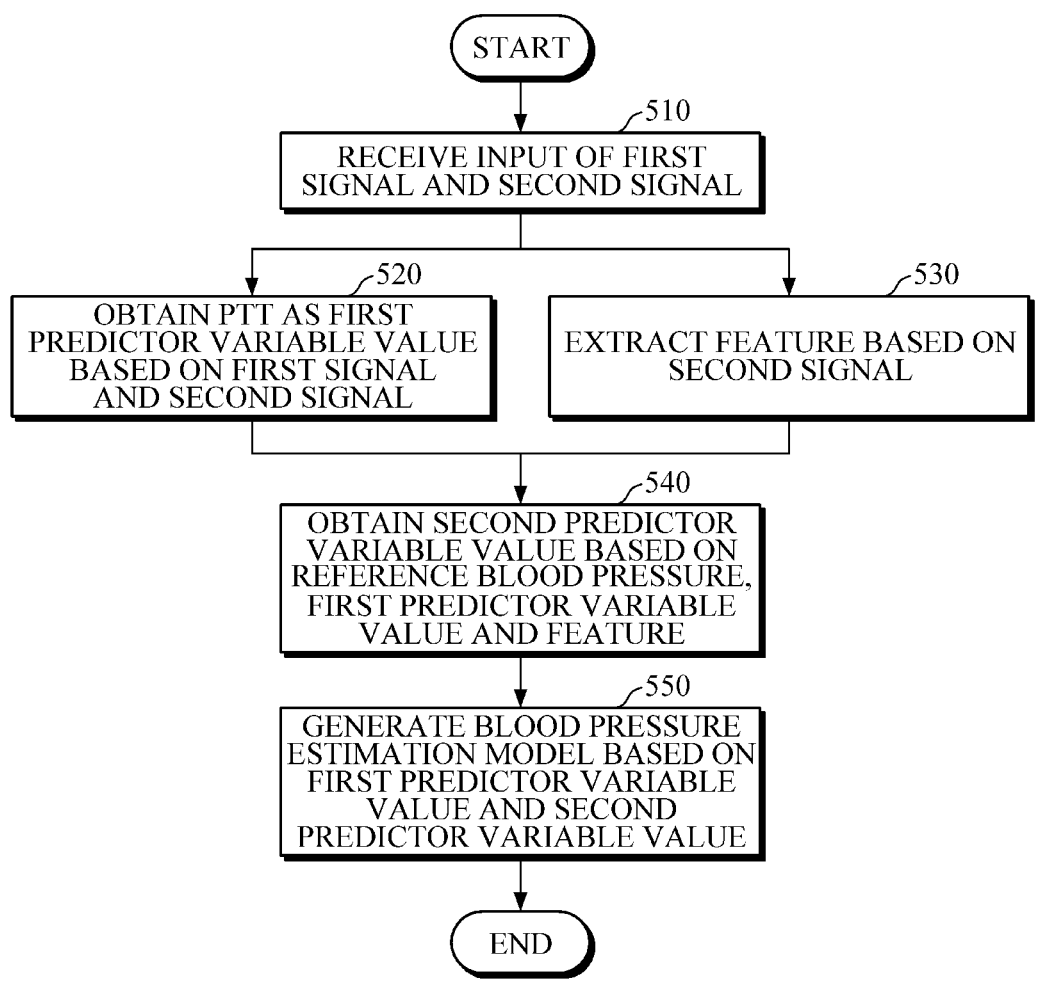
FIG. 5 is a flowchart illustrating a method of generating a blood pressure estimation model according to an example embodiment.
Figure 6A:
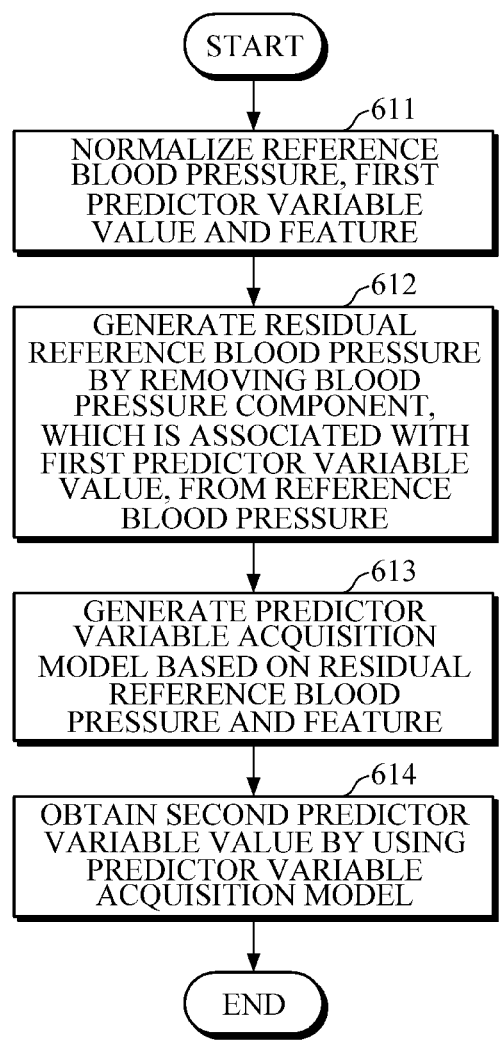
FIGS. 6A and 6B are flowcharts illustrating examples of obtaining a second predictor variable value of FIG. 5.
Figure 6B:
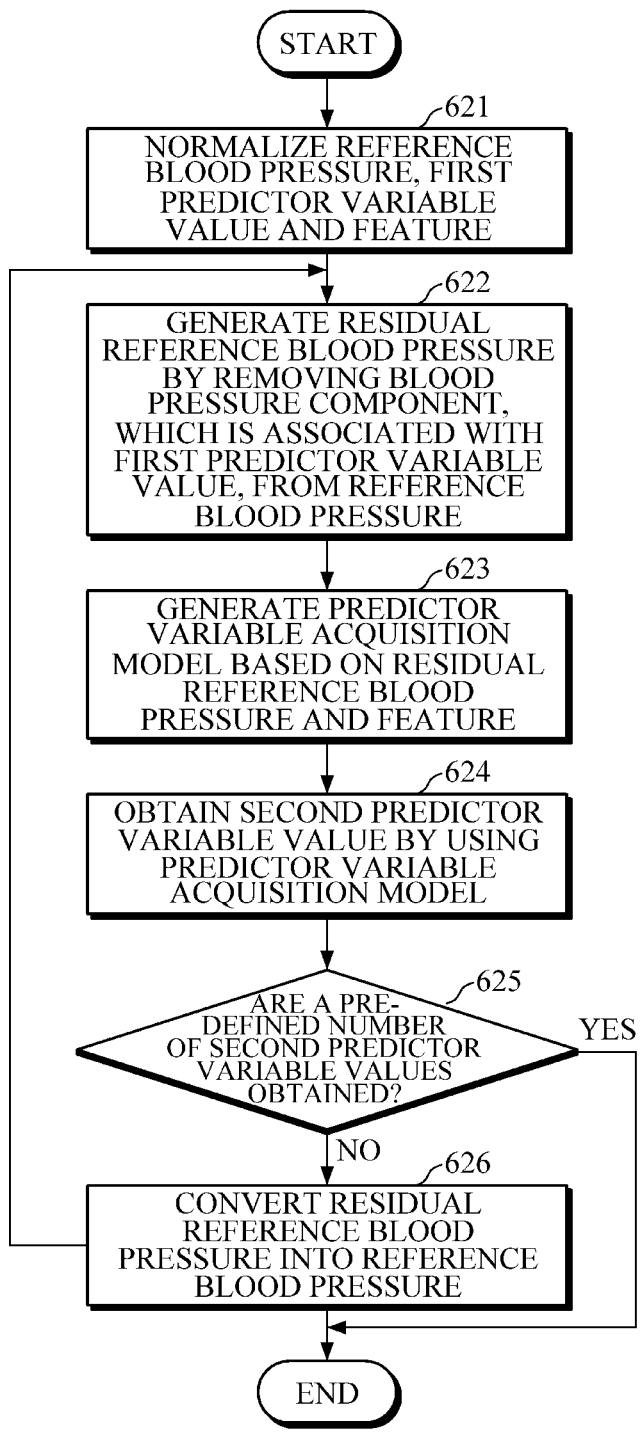

FIG. 5 is a flowchart illustrating a method of generating a blood pressure estimation model according to an example embodiment. FIGS. 6A and 6B are flowcharts illustrating examples of obtaining a second predictor variable value of FIG. 5.

Referring to FIG. 5, the method of generating a blood pressure estimation model may be performed by the apparatus 100 for generating a blood pressure estimation model, which is described in detail above, and thus will be briefly described below.

The apparatus 100 for generating a blood pressure estimation model receives an input of a first signal and a second signal in 510. The first signal may be one of an electrocardiography (ECG) signal, a photoplethysmogram (PPG) signal, an electromyography (EMG) signal, an impedance plethysmogram (IPG) signal, a pressure wave, and a video plethysmogram (VPG) signal; and the second signal may be a ballistocardiogram (BCG) signal. The first signal and the second signal may be obtained from a plurality of subjects for learning a blood pressure estimation model.

Then, the apparatus 100 for generating a blood pressure estimation model may obtain a PTT as a first predictor variable value based on the first signal and the second signal in 520. For example, if the first signal is an ECG signal and the second signal is a BCG signal, the apparatus 100 for generating a blood pressure estimation model may obtain, as the PTT, a time interval between an R-wave and a J-wave; and if the first signal is a PPG signal and the second signal is the BCG signal, the apparatus 100 for generating a blood pressure estimation model may obtain, as the PTT, a time interval between an onset point and the J-wave. However, the PTT is not limited thereto, and the apparatus 100 for generating a blood pressure estimation model may obtain, as the PTT, time intervals between any one of an H-wave, an I-wave, a K-wave, and an L-wave of the PPG signal, instead of the J-wave of the BCG signal 43, and the R-wave (R) of the ECG signal 41 and the onset point of the PPG signal 42.

Subsequently, the apparatus 100 for generating a blood pressure estimation model may extract one or more features based on the second signal in 530. For example, the apparatus 100 for generating a blood pressure estimation model may extract, as features, a J-L time interval, an I-K time interval, and a J-K time interval which are related to a change in PTT, a J-K amplitude, a K-L amplitude, and an I-J amplitude which are related to a change in pulse pressure, and a J-J time interval which is related to a heart rate.

Next, the apparatus 100 for generating a blood pressure estimation model may obtain a second predictor variable value based on the reference blood pressure, the first predictor variable value and the features in 540.

An example of obtaining the second predictor variable value will be described below with reference to FIG. 6A.

The apparatus 100 for generating a blood pressure estimation model may normalize the reference blood pressure, the first predictor variable value, and the features in 611. For example, as described above, the apparatus 100 for generating a blood pressure estimation model may normalize the values by subtracting an average of each of the values from the values, and by dividing the resulting value by the average of the respective values.

Then, the apparatus 100 for generating a blood pressure estimation model may generate a residual reference blood pressure by removing a blood pressure component, which is associated with the first predictor variable value, from the reference blood pressure in 612. For example, the apparatus 100 for generating a blood pressure estimation model may generate the residual reference blood pressure by obtaining a blood pressure component, related to the PTT, by calculating an inner product of the reference blood pressure and the PTT, and by subtracting the blood pressure, related to the PTT, from the reference blood pressure.

Subsequently, the apparatus 100 for generating a blood pressure estimation model may generate a predictor variable acquisition model based on the residual reference blood pressure and the features in 613. For example, the apparatus 100 for generating a blood pressure estimation model may generate the predictor variable acquisition model by obtaining a coupling coefficient of each feature by performing singular value decomposition of a component, which is obtained by calculating an inner product of the residual reference blood pressure and each of the features, so that a covariance between the residual reference blood pressure and each feature is maximized. In this case, the apparatus 100 for generating a blood pressure estimation model may obtain an optimal coupling coefficient for each feature by leaning based on training data of a plurality of subjects.

Next, the apparatus 100 for generating a blood pressure estimation model may obtain a second predictor variable value by using the predictor variable acquisition model in 614. For example, as represented by the above Equation 3, the apparatus 100 for generating a blood pressure estimation model may obtain the second predictor variable value by summing up all values obtained by multiplying the coupling coefficient of each of the features by the features.

Referring to FIG. 6B, an example of obtaining a plurality of second predictor variable values by performing the process of obtaining the second predictor variable values in multi-steps will be described below.

The apparatus 100 for generating a blood pressure estimation model may normalize the reference blood pressure, the first predictor variable value, and the features in 621. For example, as described above, the apparatus 100 for generating a blood pressure estimation model may normalize the values by subtracting an average of each of the values from the values, and by dividing the resulting value by the average of the respective values.

Then, the apparatus 100 for generating a blood pressure estimation model may generate a residual reference blood pressure by removing a blood pressure component, which is associated with the second predictor variable value, from the reference blood pressure in 622. For example, the apparatus 100 for generating a blood pressure estimation model may generate the residual reference blood pressure by obtaining a blood pressure component, related to the PTT, by calculating an inner product of the reference blood pressure and the PTT, and by subtracting the blood pressure component related to the PTT from the reference blood pressure.

Subsequently, the apparatus 100 for generating a blood pressure estimation model may generate a predictor variable acquisition model based on the residual reference blood pressure and the features in 623. For example, the apparatus 100 for generating a blood pressure estimation model may generate the predictor variable acquisition model by obtaining a coupling coefficient of each feature by performing singular value decomposition of a component, which is obtained by calculating an inner product of the residual reference blood pressure and each feature, so that a covariance between the residual reference blood pressure and each feature is maximized. In this case, the apparatus 100 for generating a blood pressure estimation model may obtain an optimal coupling coefficient for each feature by leaning based on training data of a plurality of subjects.

Next, the apparatus 100 for generating a blood pressure estimation model may obtain a second predictor variable value by using the predictor variable acquisition model in 624. For example, as represented by the above Equation 3, the apparatus 100 for generating a blood pressure estimation model may obtain the second predictor variable value by summing up all values obtained by multiplying the coupling coefficient of each of the features by the features.

Then, the apparatus 100 for generating a blood pressure estimation model may determine whether a pre-defined number of second predictor variable values are obtained in 625. Upon determination that a desired number of second predictor variable values are not obtained, the apparatus 100 for generating a blood pressure estimation model may determine the generated residual reference blood pressure as a new reference blood pressure in 626, and may repeat the process from the operation 622. Upon determination that a desired number of second predictor variable values are obtained, the apparatus 100 for generating a blood pressure estimation model may terminate the process.

Referring back to FIG. 5, the apparatus 100 for generating a blood pressure estimation model may generate a blood pressure estimation model based on the first predictor variable value and the second predictor variable value in 550. For example, the apparatus 100 for generating a blood pressure estimation model may obtain a coefficient for each predictor variable by training the blood pressure estimation model, as represented by the above Equation 4, using the first predictor variable values, the second predictor variable values, and the reference blood pressure values of a plurality of subjects as training data.

Figure 7:
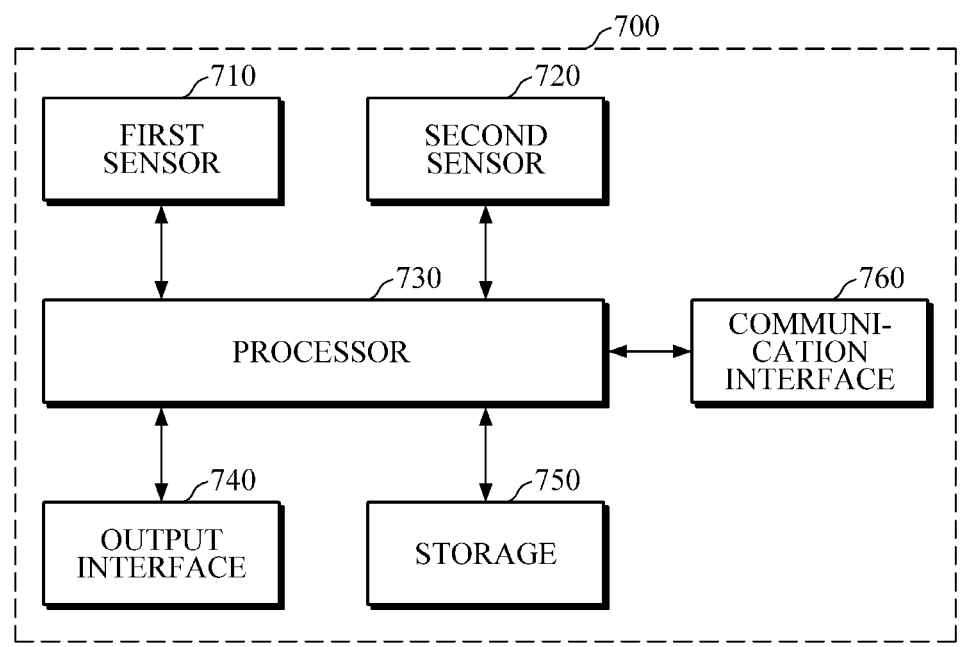
FIG. 7 is a block diagram illustrating an apparatus for estimating blood pressure according to an example embodiment.

FIG. 7 is a block diagram illustrating an apparatus for estimating blood pressure according to an example embodiment.

Referring to FIG. 7, an apparatus 700 for estimating blood pressure includes a first sensor 710, a second sensor 720, a processor 730, an output interface 740, a storage 750, and a communication interface 760.

The first sensor 710 and the second sensor 720 may be electrically connected to the processor 730, and may measure a first signal and a second signal, respectively, under the control of the processor 730. The first signal may include an electrocardiography (ECG) signal, an electromyography (EMG) signal, an impedance plethysmogram (IPG) signal, a photoplethysmogram (PPG) signal, a pressure wave, a video plethysmogram (VPG) signal, and the like. Further, the second signal may be a ballistocardiogram (BCG) signal.

In response to a request for estimating blood pressure, the processor 730 may control both the first sensor 710 and the second sensor 720 at the same time to measure the first signal and the second signal for a predetermined period of time. Upon receiving the first signal and the second signal, the processor 730 may perform preprocessing, such as band-pass filtering, smoothing, equalization of beats of continuously measured signals, and the like.

The processor 730 may obtain a first predictor variable value of a blood pressure estimation model by obtaining a PTT based on characteristic points of the first signal and the second signal. Further, the processor 730 may extract a plurality of features from the second signal, and may obtain a second predictor variable value of the blood pressure estimation model by applying the extracted plurality of features to a predictor variable acquisition model. In this case, the processor 730 may extract, for example, a J-L time interval, an I-K time interval, and a J-K time interval which are related to a change in PTT, and a J-K amplitude, a K-L amplitude, and an I-J amplitude which are related to a change in pulse pressure (PP), from the BCG signal. In addition, upon obtaining the PTT and the plurality of features, the processor 730 may normalize the obtained PTT and the plurality of features to reflect user characteristics, and may obtain the first predictor variable value and the second predictor variable value by using the normalize PTT and features.

Upon obtaining the first predictor variable value and the second predictor variable value, the processor 730 may obtain an estimated blood pressure value by using the blood pressure estimation model as represented by the above Equation 4 or Equation 5. Further, the processor 730 may evaluate a cardiovascular health condition by comprehensively analyzing whether a current estimated blood pressure value is normal, a blood pressure estimation history, and the like. The processor 730 may generate information, such as an evaluation score showing a quantified result of the cardiovascular health condition evaluation, or actions for a user to take in response to the evaluation result.

The output interface 740 may output and provide the first signal, the second signal, the estimated blood pressure value, and the result of the health condition evaluation to a user. The output interface 740 may include various output modules, such as a display, a speaker, a haptic device, and the like, and may provide the information to the user by using one or more of the various output modules.

The storage 750 may store a variety of information for estimating blood pressure. For example, the storage 750 may store a pre-defined blood pressure estimation model, a predictor variable acquisition model, and the like. The storage 750 may store the first signal and the second signal, which are measured by the first sensor 710 and the second sensor 720 respectively, the estimated blood pressure value, the result of the health condition evaluation, the blood pressure estimation history, and the like which are obtained by the processor 730, and the like. Furthermore, the storage 750 may store user characteristic information, such as a user's age, sex, health condition, and the like, which are used as base-line data for health condition evaluation, but the stored information is not limited to these examples.

The communication interface 760 may communicate with an external device to transmit and receive various data related to estimating blood pressure. For example, the communication interface 760 may receive the predictor variable acquisition model and the blood pressure estimation model from the apparatus 100 for generating a blood pressure estimation model, and may update the existing predictor variable acquisition model and blood pressure estimation model which are stored in the storage 750. Further, the communication interface 760 may transmit a blood pressure estimation result to an external device, such as a user's smartphone, tablet personal computer (PC), desktop computer, laptop computer, wearable device, and the like.

In addition, by calibrating the predictor variable acquisition model and/or the blood pressure estimation model at predetermined intervals or in response to a user's request, the processor 730 may generate and update a personalized model.

For example, the storage 750 may store a universal predictor variable acquisition model and/or a universal blood pressure estimation model, which are generated by the apparatus 100 for estimating a blood pressure estimation model at the time of manufacture of the apparatus 700 for estimating blood pressure. The processor 730 may estimate blood pressure by using the universal predictor variable acquisition model and/or blood pressure estimation model in an initial stage. Upon estimating a user's blood pressure for a predetermined period of time by using the universal predictor variable acquisition model and/or blood pressure estimation model, the processor 730 may generate a predictor variable acquisition model and a blood pressure estimation model, which are personalized for the user, by learning based on training data, such as the first signal, the second signal, the PTT, the features, the reference blood pressure, and the like which are collected from the user during the period of time. As described above, by using as training data previously accumulated data which are obtained periodically from the user during the estimation of the user's blood pressure, the processor 730 may improve accuracy of the blood pressure estimation model to be applied to the user.

Figure 8:
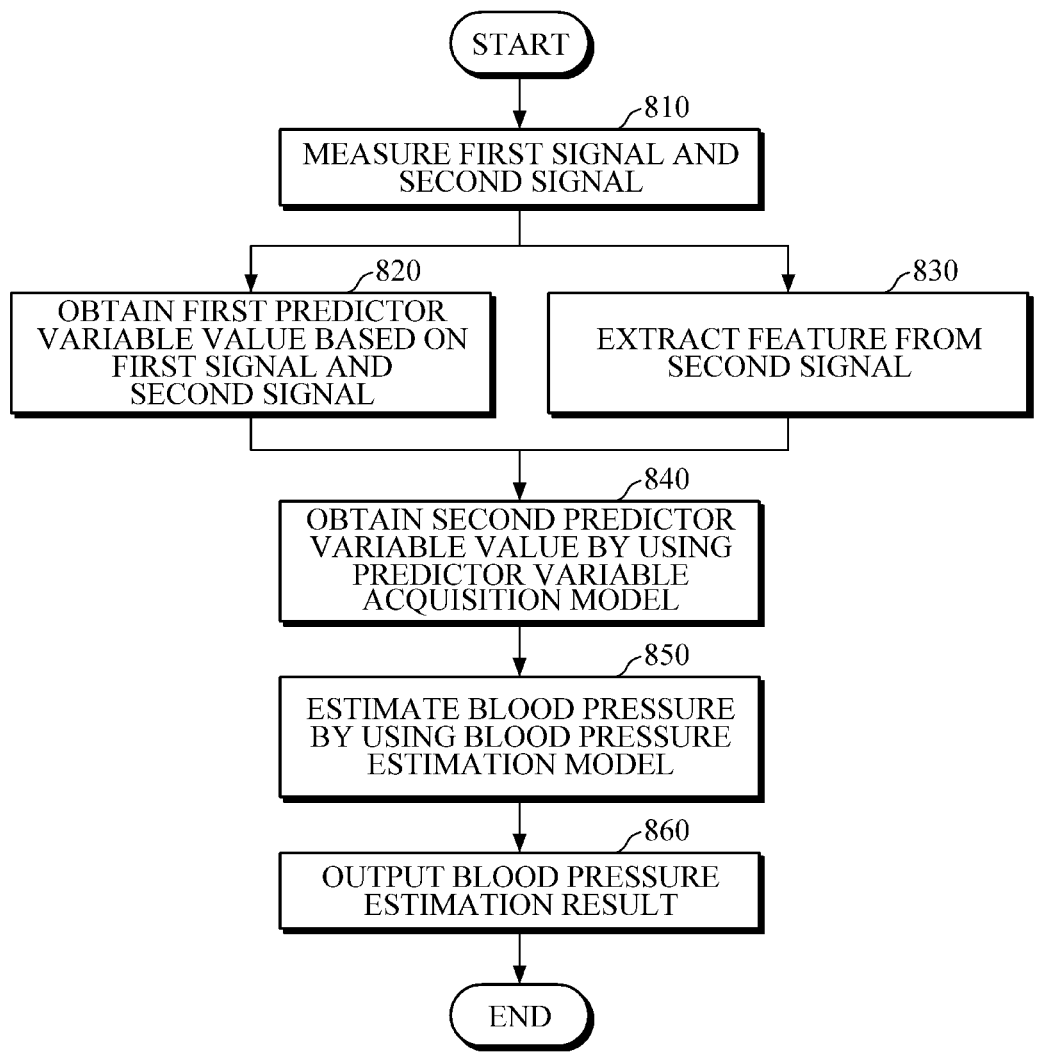
FIG. 8 is a flowchart illustrating a method of estimating blood pressure according to an example embodiment.

FIG. 8 is a flowchart illustrating a method of estimating blood pressure according to an example embodiment.

The method of FIG. 8 is an example of a method of estimating blood pressure which is performed by the apparatus 700 for estimating blood pressure, and will be briefly described below.

The apparatus 700 for estimating blood pressure may measure a first signal and a second signal from a user in 810.

Then, by obtaining a PTT based on characteristic points of the first signal and the second signal, the apparatus 700 for estimating blood pressure may obtain a first predictor variable value of a blood pressure estimation model in 820, and may extract a plurality of features from the second signal in 830.

Subsequently, the apparatus 700 for estimating blood pressure may obtain a second predictor variable value of the blood pressure estimation model by using a predictor variable acquisition model based on the extracted plurality of features in 840. In this case, the apparatus 700 for estimating blood pressure may normalize the extracted features to reflect user characteristics.

Next, upon obtaining the first predictor variable value and the second predictor variable value, the apparatus 700 for estimating blood pressure may obtain an estimated blood pressure value by using the blood pressure estimation model in 850. In this case, the apparatus 700 for estimating blood pressure may evaluate a cardiovascular health condition by comprehensively analyzing whether a current estimated blood pressure value is normal, a blood pressure estimation history, and the like.

Then, the apparatus 700 for estimating blood pressure may output the first signal, the second signal, the estimated blood pressure value, and/or a result of the health condition evaluation in 860.

Figure 9:
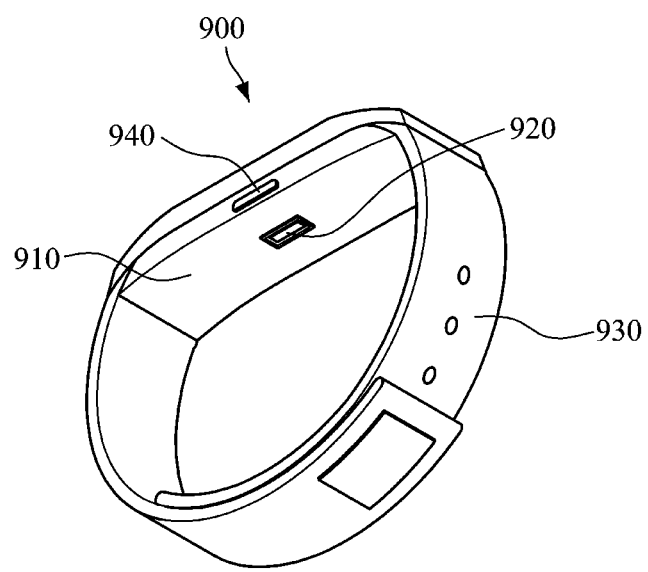
FIG. 9 is a diagram illustrating a wearable device according to an example embodiment.

FIG. 9 is a diagram illustrating a wearable device according to an example embodiment. The aforementioned embodiments of the apparatus 700 for estimating blood pressure may be mounted in a wearable device.

Referring to FIG. 9, the wearable device 900 includes a main body 910 and a strap 930.

The strap 930, which is connected to both ends of the main body 910, may be flexible so as to be bent around a user's wrist. The strap 930 may include a first strap and a second strap which are separated from each other. One ends of the first strap and the second strap are connected to the main body 910, and the other ends thereof may be connected to each other via a connecting means. In this case, the connecting means may be formed as magnetic connection, Velcro connection, pin connection, and the like, but is not limited thereto. Further, the strap 930 is not limited thereto, and may be integrally formed as a non-detachable band.

Air may be injected into the strap 930 or an airbag may be included in the strap 930, so that the strap 930 may have elasticity according to a change in pressure applied to the wrist, and the strap 930 may transmit the change in pressure of the wrist to the main body 910.

A battery may be embedded in the main body 910 or the strap 930 to supply power to various modules of the wearable device 900.

The main body 910 may include a sensor 920, which is mounted on one side thereof. The sensor 920 may include a PPG sensor which measures a PPG signal. The PPG sensor may include a light source which emits light onto the skin of the wrist; and a detector, such as a contact image sensor (CIS) optical sensor, a photodiode and the like, which detects light scattered or reflected from the wrist. In addition, the sensor 920 may further include an acceleration sensor or a force sensor for measuring a BCG signal from the object.

A processor may be mounted in the main body 910, and may be electrically connected to various modules mounted in the wearable device 900. The processor may obtain a PTT by using the PPG signal and the BCG signal measured by the sensor 920, may extract a plurality of features from the BCG signal, and may estimate blood pressure based on the PTT and the features. A detailed description thereof will be omitted.

Further, the main body 910 may include a storage which stores reference information for estimating blood pressure and performing various functions of the wearable device 900, and information processed by various modules.

In addition, the main body 910 may also include a manipulator 940 which is mounted on one side thereof, and receives a user's control command and transmits the received control command to the processor. The manipulator 940 may include a power button to input a command to turn on/off the wearable device 900.

Furthermore, a display for outputting information to a user may be mounted on a front surface of the main body 910. The display may include a touch screen for receiving touch input. The display may receive a touch input from a user, may transmit the received touch input to the processor, and may display a processing result of the processor.

Moreover, a communication interface, provided for communication with an external device, may be mounted in the main body 910. The communication interface may transmit a blood pressure estimation result to an external device, e.g., a user's smartphone, and may receive a blood pressure estimation model from the apparatus for generating a blood pressure estimation model.

Figure 10:
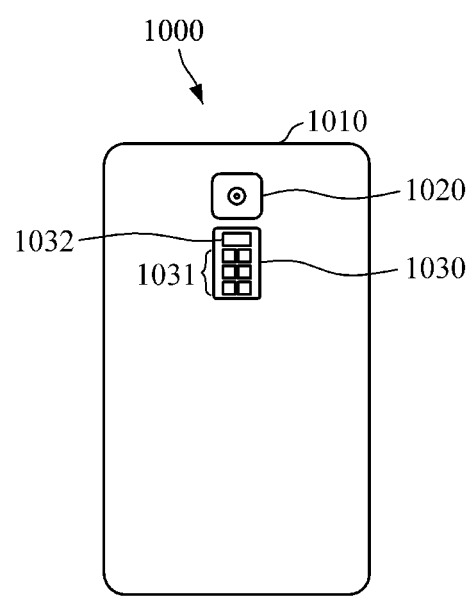
FIG. 10 is a diagram illustrating a smart device according to an example embodiment.

FIG. 10 is a diagram illustrating a smart device according to an example embodiment. The smart device may be a smartphone, a tablet PC, and the like, and may include the function of the aforementioned apparatus 700 for estimating blood pressure.

Referring to FIG. 10, the smart device 1000 includes a main body 1010 and a sensor 1030 mounted on one surface of the main body 1010. The sensor 1030 may include a PPG sensor including a light source 1031 and a detector 1032. The sensor 1030 may further include a force sensor or an acceleration sensor for measuring a BCG signal. The detector 1032 may include a photodiode, a CIS optical sensor, and the like.

Further, a display may be mounted on a front surface of the main body 1010. The display may visually display a blood pressure estimation result, a health condition evaluation result, and the like. The display may include a touch screen, and may receive information input through the touch screen and transmit the received information to the processor.

Moreover, an image sensor 1020 may be mounted in the main body 1010 as illustrated in FIG. 10. The image sensor 1020 captures various images, for example, an image of a finger touching the sensor 1030. If a contact image sensor (CIS) 1032 is mounted in a first sensor of the sensor 1030, the image sensor 1020 may be omitted.

As described above, the processor may estimate blood pressure based on the PPG signal and the BCG signal which are measured by the sensor 1030. A detailed description thereof will be omitted.

Figure 11A:
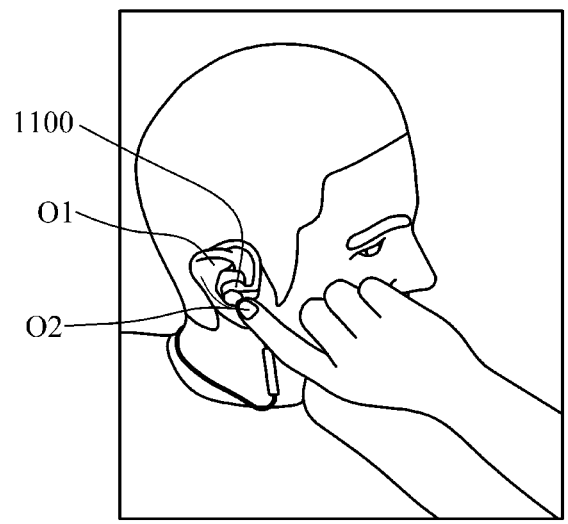
FIGS. 11A, 11B, and 11C are diagrams illustrating an earphone according to an example embodiment.
Figure 11B:
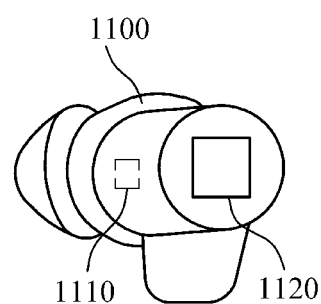
Figure 11C:
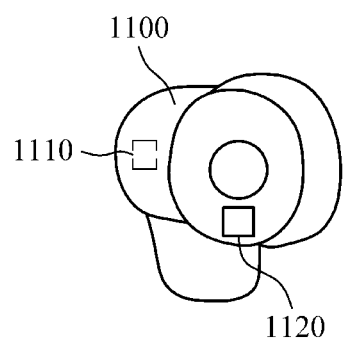

FIGS. 11A, 11B, and 11C are diagrams illustrating an earphone according to an example embodiment. Various example embodiments of the aforementioned apparatus 700 for estimating blood pressure may be mounted in a device, such as an earphone illustrated in FIGS. 11A to 11C. Here, the earphone includes a wired or wireless earphone, and may be an earbud-type earphone, a necklace-type earphone, an earring-type earphone, and the like, with no limitation on the type of earphones.

Referring to FIGS. 11A and 11B, when a user inserts an earphone 1100 into an ear 01 and touches the earphone 1100 with a finger 02, a PPG signal and a BCG signal may be measured, and blood pressure may be estimated by using the measured PPG signal and BCG signal. For example, referring to FIG. 11B, a BCG sensor 1110 for measuring the BCG signal may be mounted in the earphone 1100. Further, a PPG sensor 1120 may be disposed on an outer side of the earphone 1100 to measure the PPG signal from the finger being in contact with the earphone 1100 while the earphone 1100 is inserted into the ear. In this case, the BCG sensor 1110 and the PPG sensor 1120 may be disposed on both the right and left sides of the earphone 1100 or on any one side thereof.

Referring to FIG. 11C, the PPG signal and the BCG signal may be measured at the same time while the user inserts the earphone 1100 into the ear. For example, the BCG sensor 1110 for measuring the BCG signal may be mounted inside the earphone 1100, and the PPG sensor 1120 may be disposed on an inner side of the earphone 1100 to measure the PPG signal inside the ear being in contact with the earphone 1100 while the earphone 1100 is inserted into the ear. In this case, the BCG sensor 1110 and the PPG sensor 1120 may be disposed on both the right and left sides of the earphone 1100 or on any one side thereof.

Further, a processor for performing the function of estimating blood pressure may be mounted in the earphone 1100 or in an earphone controller. In this case, when the earphone 1100 is inserted into the ear, the processor controls the BCG sensor and the PPG sensor, and estimates blood pressure by using the BCG signal and the PPG signal as described above. The processor may transmit a blood pressure estimation result to an external device, e.g., a smartphone or a wearable device, which is connected by wire or wirelessly to the processor.

In addition, instead of being mounted in the earphone 1100, the processor for performing the function of estimating blood pressure may be mounted in an external device, e.g., a smartphone or a wearable device, which is connected by wire or wirelessly to the earphone 1100. The processor of the external device may receive the BCG signal and the PPG signal from the BCG sensor 1110 and the PPG sensor 1120 of the earphone 1100, and may estimate blood pressure by using the received signals.

The processor of the external device or the earphone 1100 may visually output the blood pressure estimation result to the user through a display of the external device. Alternatively, when the earphone 1100 is worn on the ear, the processor may output the blood pressure estimation result by sound (e.g., voice) through the earphone 1100 upon completing estimation of blood pressure.

According to the example embodiments, blood pressure may be accurately estimated by pulse transit time (PTT) analysis and pulse wave analysis (PWA) using a ballistocardiogram (BCG) signal without a cuff.

The disclosure may be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments for implementing the disclosure may be easily deduced by programmers of one of ordinary skill in the art.

The disclosure has been described herein with regard to preferred embodiments. However, it will be obvious to those skilled in the art that various changes and modifications can be made without changing technical ideas and essential features of the disclosure. Thus, it is clear that the above-described embodiments are illustrative in all aspects and are not intended to limit the disclosure.

What is claimed is:

1. An apparatus for monitoring a blood pressure of a user, the apparatus comprising:
    a first sensor configured to measure a first signal from a user;
    a second sensor configured to measure a second signal from the user;
    a processor configured to obtain a pulse transit time (PTT) as a first predictor variable value based on the first signal and the second signal, configured to extract at least one feature from the second signal, configured to obtain a second predictor variable value based on the extracted at least one feature and a reference blood pressure, and configured to, by using training data comprising first signals, second signals, and reference blood pressures obtained for a plurality of users, generate a blood pressure estimation model based on the first predictor variable value and the second predictor variable value, wherein the blood pressure estimation model is used to estimate a blood pressure without a cuff; and
    a display configured to display the estimated blood pressure obtained from the blood pressure estimation model,
    wherein the processor is further configured to generate a predictor variable acquisition model based on the reference blood pressure, the first predictor variable value, and the at least one feature, and obtain the second predictor variable value by using the predictor variable acquisition model, and
    wherein the processor is further configured to (i) generate a residual reference blood pressure by removing a component, which is related to the first predictor variable value, from the reference blood pressure, and (ii) generate the predictor variable acquisition model based on the residual reference blood pressure.

2. The apparatus of claim 1, further comprising a communication interface configured to receive at least one of the first signal and the second signal from an external device.

3. The apparatus of claim 2, wherein the first signal comprises at least one of an electrocardiography (ECG) signal, a photoplethysmogram (PPG) signal, an electromyography (EMG) signal, an impedance plethysmogram (IPG) signal, a pressure wave, and a video plethysmogram (VPG) signal; and wherein the second signal comprises a ballistocardiogram (BCG) signal.

4. The apparatus of claim 1, wherein the processor is further configured to, based on the first signal being a PPG signal and the second signal being a BCG signal, obtain, as the PTT, a time interval between an onset point of the PPG signal and any one of a J-wave, an H-wave, an I-wave, a K-wave, and an L-wave of the BCG signal, or wherein the processor is further configured to, based on the first signal being an ECG signal and the second signal being the BCG signal, obtain, as the PTT, a time interval between an R-wave of the ECG signal and any one of the J-wave, the H-wave, the I-wave, the K-wave, and the L-wave of the BCG signal.

5. The apparatus of claim 1, wherein the at least one feature comprises at least one of an I-J time interval, a J-L time interval, an I-K time interval, a J-K time interval, a J-K amplitude, a K-L amplitude, and an I-J amplitude of the second signal.

6. The apparatus of claim 1, wherein the processor is further configured to preprocess the first signal and the second signal.

7. The apparatus of claim 1, wherein the processor is further configured to normalize the reference blood pressure, the first predictor variable value, and the at least one feature.

8. The apparatus of claim 1, wherein the processor is further configured to remove the component, which is related to the first predictor variable value, by subtracting a value, obtained by calculating an inner product of the reference blood pressure and the first predictor variable value, from the reference blood pressure.

9. The apparatus of claim 8, wherein the processor is further configured to generate the predictor variable acquisition model by using singular value decomposition (SVD) based on the residual reference blood pressure and the at least one feature.

10. The apparatus of claim 9, wherein the processor is further configured to perform singular value decomposition of a component, which is obtained by calculating an inner product of the residual reference blood pressure and the at least one feature, so that a covariance between the residual reference blood pressure and the at least one feature is maximized.

11. The apparatus of claim 1, wherein, in (ii) generating the predictor variable acquisition model, the processor is configured to (ii) generate the predictor variable acquisition model by using singular value decomposition (SVD) based on the residual reference blood pressure wherein the processor is further configured to (iii) obtain the second predictor variable value by using the predictor variable acquisition model, and wherein the processor is further configured to determine the residual reference blood pressure as a next reference blood pressure and repeatedly perform operations (i)-(iii), until a predetermined number of second predictor variable values are obtained.

* * * * *